Figure 1:
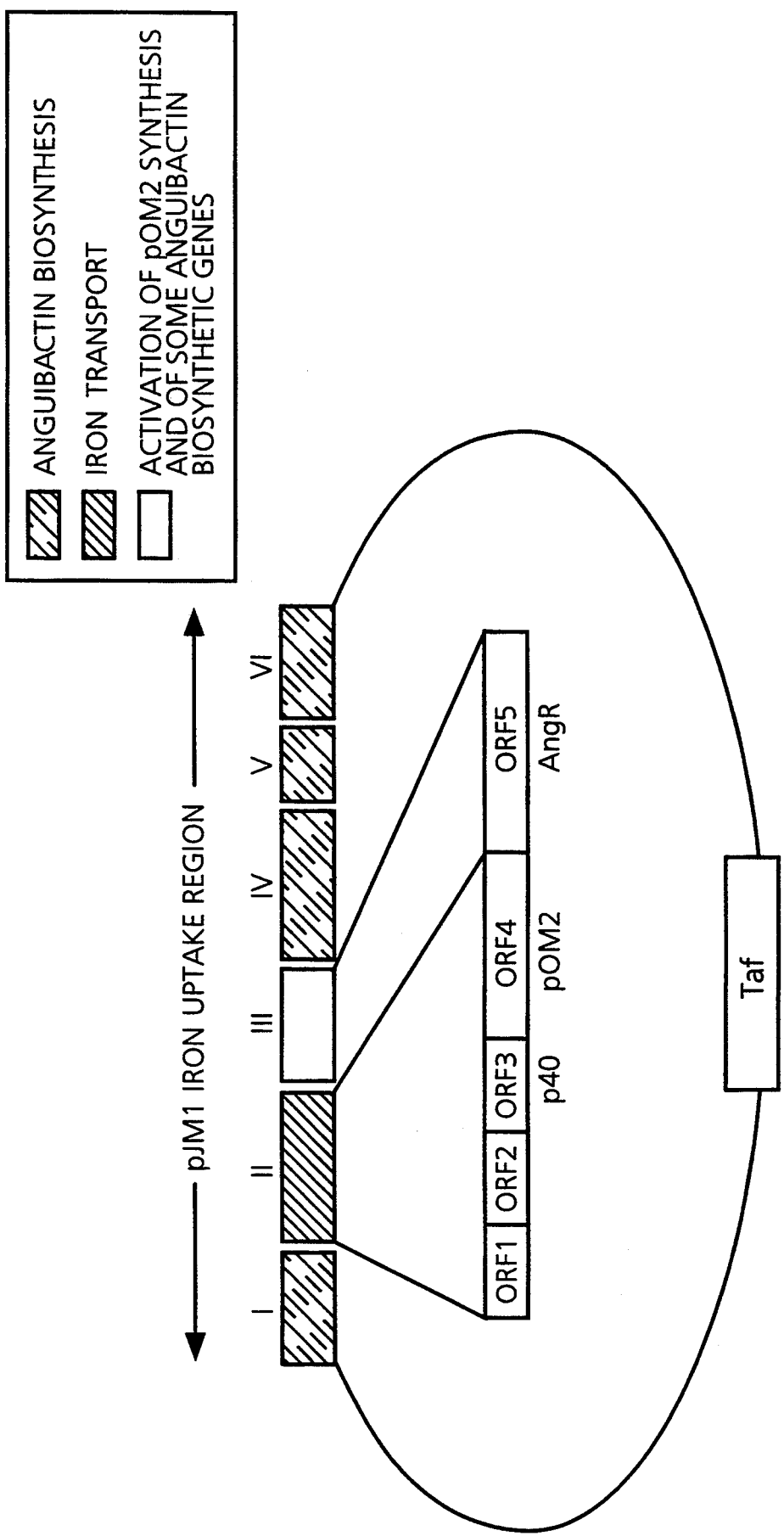

United States Patent [19]

Crosa

[11] Patent Number: 5,393,777
[45] Date of Patent: Feb. 28, 1995

[54] DEFERRATION USING ANGUIBACTIN SIDEROPHORE

[75] Inventor: Jorge H. Crosa, Tualatin, Oreg.

[73] Assignee: State of Oregon Acting by and through the State Board of Higher Education on behalf of Oregon Health Sciences University, Eugene, Oreg.

[21] Appl. No.: 614,231

[22] Filed: Nov. 15, 1990

[51] Int. Cl.⁶ ............................................. A61K 31/295
[52] U.S. Cl. ..................................................... 514/502
[58] Field of Search .......................................... 514/502

[56] References Cited

U.S. PATENT DOCUMENTS

| | | | |
|---|---|---|---|
| 3,118,823 | 1/1964 | Gaeumann et al. | 435/121 |
| 3,153,621 | 10/1964 | Gaeumann et al. | 435/121 |
| 4,530,963 | 7/1985 | DeVoe et al. | 525/54.1 |
| 4,585,559 | 4/1986 | DeVoe et al. | 210/679 |
| 4,666,927 | 5/1987 | Hider et al. | 514/350 |

OTHER PUBLICATIONS

Chemical Abstracts (105: 130412h) 1986.
Chemical Abstracts (109: 67801z) 1988.
Tolmasky, et al., "Increased Production of the Siderophore Anguibactin Mediated by pJM1-Like Plasmids in Vibrio anguillarum," *Infection and Immunity* 56:1608–1614 (Jun., 1988).

*Primary Examiner*—Marianne M. Cintins
*Assistant Examiner*—K. Weddington
*Attorney, Agent, or Firm*—Klarquist Sparkman Campbell Leigh & Whinston

[57] ABSTRACT

Methods for removing ferric iron from aqueous liquids and for performing deferration therapy are disclosed, involving the use of a novel siderophore, termed anguibactin. Anguibactin is isolated from a marine pathogen, *Vibrio anguillarum*, containing the pMJ1 plasmid. Anguibactin inhibits iron uptake by living cells, wrests iron from vertebrate tissues, removes iron from other siderophores and ferric hydroxide, and removes ferric iron from aqueous solutions, including cell-culture media. For deferration therapy, anguibactin from which bound iron has been removed is administered by dissolving in water or other liquid aqueous pharmaceutical carrier at a dosage typical for other siderophores. Anguibactin is preferably administered intramuscularly or subcutaneously, but can be given intravenously. Oral administration is also possible, particularly if the siderophore is encapsulated in a form allowing it to pass intact through the acidic environment of the stomach but become available for absorption in the intestine. This siderophore has the advantages of low molecular weight, extremely high affinity for ferric iron, and non-use by any known human pathogen. The structure is amenable to immobilization on a solid substrate.

7 Claims, 3 Drawing Sheets

DEFERRATION USING ANGUIBACTIN SIDEROPHORE

This invention was funded in part by Public Health Service Grant No. AI19018 from the National Institute of Allergy and Infectious Diseases, National Institutes of Health. The government has rights in this invention.

FIELD OF THE INVENTION

This invention relates to removing ferric iron from aqueous liquids using novel compositions of matter. In particular, it relates to using a novel siderophore for deferration therapy and other related applications.

BACKGROUND OF THE INVENTION

It has been known for years that many bacteria require iron for growth. At least some types of bacteria and fungi obtain the iron they need by producing special compounds termed "siderophores" (Greek for "iron bearers") which are relatively low molecular-weight (less than about 1000 daltons) iron-binding ("iron chelating") compounds. Generally, siderophores are ferric-specific ligands, the natural purpose of which is to supply iron to the microorganism cells. Each of the several species of siderophores is a key component in the iron high-affinity system of the respective microorganism that includes specific membrane-associated receptors.

Representative siderophores include phenolate compounds such as "agrobactin" from *Agrobacterium tumefaciens* and "pseudobactin" from Pseudomonas, and hydroxamates such as "schizokinin" from *Bacillus megaterium* and ferrioxamines from Actinomyces. Siderophores produced by fungi include hydroxamates such as ferrichromes from Penicillium species, rhodotorulic acids from Rhodoturula, and other hydroxamates from certain Ectomycorrhiza species. See Neilands, *Ann. Rev. Biochem.* 50:715–731 (1981).

Host animals such as mammals and fish produce iron-binding proteins, including ferritin, transferrin, and hemosiderin, which tightly sequester ionic iron in the body. As a result, unbound or "free" iron (as ferrous or ferric ions) is present only at very low concentrations in a healthy host's plasma and other body fluids.

Siderophore production enables invading bacteria to successfully compete with the host's iron-binding proteins for iron in the host's body that would otherwise be unavailable to the bacteria. Without an ability to wrest bound iron from the host, bacteria would be unable to proliferate sufficiently to cause disease. Hence, production of siderophores is a key to bacterial pathogenicity.

A number of diseases in humans are demonstrative of the toxicity of free iron in the body. In general, the term "hypersiderosis" represents any of several disease conditions in which the normal iron-carrying capacity of a person's blood and tissue proteins is exceeded and pathological effects due to iron overload are manifest. In such conditions, the excess iron can become deposited in various tissues, such as the myocardium and liver.

Acute iron intoxication usually results from accidental over-ingestion of iron supplements, particularly by young children. Industrial accidents can also result in acute iron intoxication.

Chronic iron overload encompasses a variety of diseases where iron accumulates in the body due to various causes. For example, intestinal control of iron absorption may be ineffective so that inappropriate amounts of dietary iron are allowed to enter the body (e.g., idiopathic hemochromatosis and anemias with ineffective erythropoiesis). In such cases, iron overload develops even when a normal diet is consumed. Hemochromatosis can also occur in alcoholics with cirrhosis. Long-term exposure to a diet containing excessive iron can lead to iron overload in otherwise normal subjects (dietary iron overload). In addition, large amounts of parenteral preparations of iron inappropriately prescribed, or repeated blood transfusions for refractory anemias, may result in the accumulation of excess iron in the body (transfusional siderosis). The iron liberated from the transfused cells cannot be excreted and it accumulates in the cells of the reticuloendothelial system and in cardiac muscle, kidneys, thyroid gland and adrenal gland. Changes in iron distribution from the primary reticuloendothelial iron to parenchymal iron overload are ascribed to the high saturation of transferrin, which provides favorable conditions for uptake of iron by parenchymal cells. Free transferrin thus protects the tissues from siderosis.

An example of a hereditary disease characterized by chronic iron overload is Cooley's anemia (thallasemia major), where congestive heart failure often precedes rapid deterioration and death of the untreated patient almost always in early infancy.

Electrocardiogram abnormalities are the most frequent manifestations of the cardiomyopathy of hemochromatosis. In descending order of frequency, these are T-wave flattening and inversion, low-voltage tracings, arrhythmias both superventricular (notable auricular fibrillation) and/or ventricular (premature ventricular contractions which may precede ventricular tachycardia or ventricular fibrillation). Congestive heart failure is rarer, but may be fatal, especially in young subjects. Postmortem examination of the heart shows fibrosis and hemosiderin deposits which are greater in the ventricles than in the atria, greater on the left side than the right side, and greater in the epicentrum than in the endocardium. Iron chelation therapy offers the possibility of alleviating this harmful and potentially lethal accumulation of iron in cardiac tissue.

Virtually the only iron chelator or siderophore currently in pharmacological use is deferoxamine (DESFERAL from CIBA Pharmaceuticals; U.S. Pat. Nos. 3,118,823 and 3,153,621). Deferoxamine was originally isolated from *Streptomyces pilosus*. This drug chelates iron by forming a stable complex with an iron atom. The complex prevents the iron from entering into further chemical reactions. The drug has a high affinity for ferric iron ($K_a = 10^{31}$) coupled with a very low affinity for calcium ($K_a = 10^2$). Deferoxamine wrests iron from ferritin and hemosiderin but not readily from transferrin and substantially not at all from cytochromes and hemoglobin. Theoretically, deferoxamine is capable of binding about 8.5 parts by weight of ferric iron. The molecular weight of deferoxamine is 657 g/mol.

Deferoxamine has improved the prognosis for iron-overload patients. However, this drug has certain drawbacks. First, the drug is prone to acid hydrolysis and poorly absorbed after oral administration, requiring parenteral administration, which is particularly inconvenient for long-term therapy. Second, it becomes effective when the body's iron load is at least about ten times normal, which is a level at which iron-binding proteins in the body are saturated and toxic free iron is circulating in the body. Third, it is expensive to produce. At the present time, the cost of sufficient deferoxamine for a year's treatment of chronic iron overload is several thousand dollars. Fourth, deferoxamine is toxic and can cause a number of reactions, including allergic reactions: pruritis, wheals, rash, and anaphylaxis; and dysuria, gastrointestinal symptoms, diarrhea, fever, leg cramps, hypotension, and tachycardia. Intravenous $LD_{50}$ values are 287 mg/kg in mice; 329 mg/kg in rats.

Another major disadvantage of deferoxamine is its use by certain microorganisms to enhance their pathogenicity in humans. For example, iron overload increases the susceptibility of patients to *Yersinia enterocolitica* infections. In some cases, treatment with deferoxamine has enhanced this susceptibility, resulting in generalized infections by providing this bacterium with a siderophore otherwise missing. In such cases, deferoxamine treatment must be discontinued until the infection is resolved.

Examples of siderophores that have not achieved the pharmaceutical popularity of deferoxamine include catechol derivatives as disclosed in U.S. Pat. Nos. 4,530,963 and 4,585,559 to DeVoe et al., and hydroxypyridone derivatives as disclosed in Hider et al., U.S. Pat. No. 4,666,927.

Hence, there is a need for a new pharmacological method for reducing the concentration of ferric iron in the body, for treating iron overload and related diseases, particularly by using a new siderophore that is relatively non-toxic, producible at low cost, and not utilizable by any known human pathogens.

SUMMARY OF THE INVENTION

The above-stated need is addressed by the pharmacological use of anguibactin, a siderophore having an unusual chemical structure produced by a marine pathogen, *Vibrio anguillarum*. Anguibactin is producible in large quantities at low cost as a result of the cloning of a plasmid comprising a normal iron-uptake region of *V. anguillarum*. Anguibactin is resistant to acid hydrolysis at an acid pH as low as 3 and is soluble in water and methanol.

Anguibactin inhibits iron uptake by living cells, as determined in experiments using diploid human fibroblasts and rat heart cells. Anguibactin is also able to wrest iron from the tissues of a fish host sufficient for growth and virulence of *V. anquillarum* and to remove iron from other siderophores such as aerobactin, and transferrin, as well as from ferric hydroxide. Anguibactin also apparently has very low toxicity, has a molecular weight about half that of deferoxamine and appears to chelate ferric iron more strongly than deferoxamine. Anguibactin is also capable of removing ferric iron from aqueous solutions, including cell-culture medium.

For deferration therapy, the dose regimen of anguibactin would typically start out high and be reduced as therapy progresses. Initial dosages would be within the range of 0.1 to 5 g, preferably about 0.5 to 2.5 g, which is the customary range of siderophore dosages for human use, depending in part upon the age, weight, and degree of iron intoxication of the patient. For example, a 200-pound person would initially receive a dose of about 11 mg/kg, followed by doses every 4–6 hours thereafter of about 5.5 mg/kg. Veterinary dosages would be based on g/kg weight ratios similar to those for humans. Prior to pharmacogical use, bound ferric iron should be removed from the siderophore to ensure maximal chelating capacity of the dose, which can be performed by subjecting ferrated anguibactin to a reducing agent serving to reduce the chelated ferric ion to a ferrous ion.

To protect orally administered anguibactin against acid hydrolysis in a subject's stomach, anguibactin can be rendered resistant to acid attack by encapsulating in microcapsules able to pass intact through the stomach and yet disintegrate upon reaching the neutral or slightly alkaline environment of the subject's intestine where absorption of the drug into the subject's body occurs.

Anguibactin has a chemical structure amenable to immobilizing the anguibactin molecules on a solid substrate so as to employ the siderophore in columns and the like for deferration of liquids including body fluids.

It is accordingly one object of the present invention to provide an improved method for reducing the concentration of ferric iron in an aqueous medium contacting a population of living eukaryotic cells.

Another object of the present invention is to provide a method for inhibiting the uptake of ferric iron by a population of living eukaryotic cells.

Another object of the present invention is to provide an improved method for reducing the concentration of ferric iron in the body of a vertebrate animal subject.

Another object of the present invention is to provide an improved method for removing ferric iron from a liquid.

BRIEF DESCRIPTION OF THE DRAWING

FIG. 1 is a genetic map of the iron-uptake region of the pJM1 plasmid present in virulent strains of *Vibrio anguillarum.*

FIG. 2 is a schematic depiction of the structural formula of anguibactin.

FIG. 3 is a plot showing that anguibactin inhibits uptake, from a liquid medium, of iron by cultured human diploid fibroblast cells.

DETAILED DESCRIPTION

Virulent strains of the fish pathogen *Vibrio anguillarum* are able to produce a distinctive water-soluble siderophore termed "anguibactin". Actis et al., *J. Bacteriol.* 167:57 (1986); Crosa et al., in Helinski et al. (eds.), *Plasmids in Bacteria,* pp. 759–774, Plenum, N.Y. (1985). Anguibactin is very efficient in removing iron from aqueous solution as well as from transferrin and from other iron-binding proteins in the fish host. The discovery of this siderophore resulted from the observation that the main difference between virulent and non-virulent strains was the ability of the former to grow invasively at low concentrations of iron.

Virulent strains of *Vibrio anguillarum,* which cause a terminal hemorrhagic septicemia in fish, possess a 65 kbp (65000 base pairs) plasmid named pMJ1 absent from non-virulent strains. Mutational studies established that pMJ1 carries the genes for an inducible high-efficiency iron uptake system which facilitates virulence. This iron-uptake system is induced in pMJ1-containing strains during growth under iron-limited conditions. Induction of the system results in the energy-dependent uptake of iron by the *V. anguillarum* cells.

Cloning of pMJ1 Plasmid Comprising Anguibactin Genetic Elements

The plasmid pMJ1 has now been cloned, the genetic map of the iron-uptake region of which is shown in FIG. 1. The genetic units I–VI comprising the iron-uptake region, occupying about 25 kilobase pairs (kbp)

of pMJ1, were defined by transposition mutagenesis as reviewed in Crosa, *Microbiol. Rev.*, Dec. 1989, pp. 517–530. The iron-uptake system includes an 86-kilodalton (kDa) outer membrane protein pOM2, the presence of which is associated with the acceptance and transport of iron into the cell cytosol. The pOM2 protein is missing from strains unable to grow in media in which iron is complexed by nonassimilable iron chelators, even when the strains are supplied with additional anguibactin purified from wild-type cells.

As seen in FIG. 1, anguibactin synthesis is encoded by genetic units I, IV, V, and VI. The ORF5 region (genetic unit III) encodes a regulatory protein which functions in a complex scheme for expression of the iron-uptake system, as detailed in Crosa, *Microbiol. Rev.*, December 1989, pp. 517–530.

Cloning of pJM1 has permitted anguibactin to be produced in large quantities at relatively low cost.

Culture of *V. anguillarum*

Cells of *Vibrio anguillarum* 775 were grown for 48 hours in M9 minimal medium, Crosa, *Nature (London)* 283:566–568 (1980), containing 100 μM of the nonassimilable iron chelator nitriloacetic acid. To remove traces of contaminating metals, medium salts were passed through a Chelex 100 column prior to use. Bacteria were separated from the medium by centrifugation at 7,000×g. Supernatants were stored at −20° C.

Purification of Anguibactin

Anguibactin was isolated from *V. anguillarum* 775 supernatants by adsorption onto XAD-7 macroreticular resin (Rohm and Haas). This resin was subjected to sequential Soxhlet extractions with methanol, acetonitrile, and diethylether to remove residual organic impurities prior to being packed into a column in water. The pH of culture supernatants was adjusted to neutrality to avoid coadsorption of low-molecular-weight organic acids. A 10-liter volume of supernatant was then applied to the packed XAD-7 column (5 by 10 cm) at a rate of 10 bed volumes per hour. The column was rinsed with two void volumes of deionized water, followed by a step gradient of one void volume each of 1:2 and 2:1 (v/v) methanol:water mixtures. Adsorbed material in the column was eluted with pure methanol. The peak column fractions containing anguibactin were evaporated at reduced pressure, and the residue was dissolved in 3 mL of methanol. This material was then applied to a column (1.5 by 80 cm) of Sephadex LH-20 (Pharmacia) and eluted with methanol at 0.6 mL/min. Peak fractions from the LH-20 column were reduced to dryness by rotary evaporation followed by exposure to high vacuum for one hour and stored under nitrogen at −20° C.

Biologically active anguibactin was assayed in supernatants and column fractions from the size of a growth halo around a 7-mm diameter sterile filter disk on an agarose plate containing M9 minimal medium plus 15 μM EDDA [ethylenediamine-di(o-hydroxyphenylacetic acid)] that had been seeded with 0.1 mL of an overnight culture of $10^8$ cells of *V. anguillarum* strain 775::Tn1-5. This mutant strain contains the mutant plasmid pJHC-91 (explained infra), which is receptor-proficient but siderophore-deficient. A control for siderophore specificity was the lack of a growth halo with strain H775-3 which is missing the pJM1 plasmid (explained infra) and is therefore deficient in receptor as well as siderophore activity. Typically, 5 μL of the test solution was spotted on the filter disk and allowed to dry before the disk was applied to the agarose plate. The diameter of the halo was measured after growth for 24 to 48 hours at 25° C., and that value was corrected by subtracting the 7-mm contribution from the filter disk.

Anguibactin concentrations in column fractions were quantified by measuring the strong UV absorbance of the siderophore in acidic iron perchlorate. Methanolic solutions were evaporated to dryness under a stream of $N_2$ and dissolved in 0.5 mL of deionized water, and then 0.5 mL of 5 mM $FeCl_3$ in 0.14M $HClO_4$ was added. The absorbance of the assay solution at 307 nm (the adsorption maximum of anguibactin) was measured against a blank reference containing water:$FeCl_3$-$HClO_4$ (1:1).

Structure and Properties of Anquibactin

Figure 2:
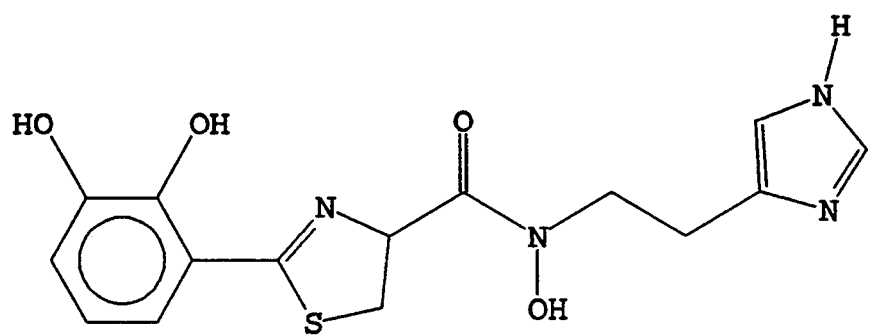
Figure 3:
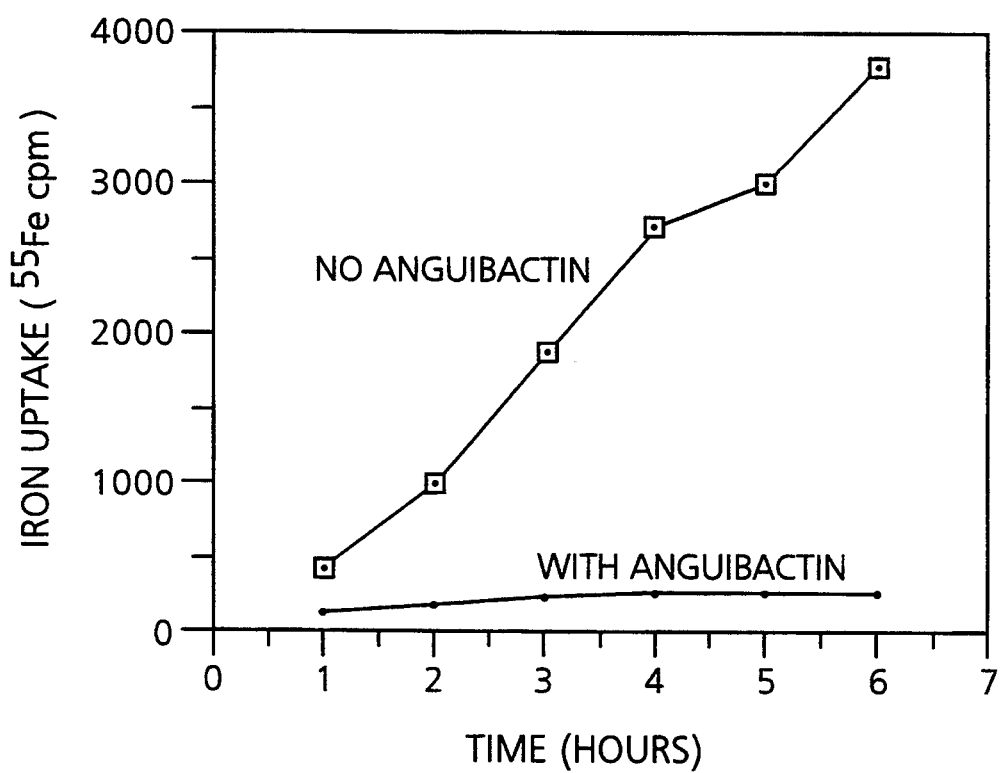

The structure of anguibactin was determined as outlined in Jalal et al., *J. Am. Chem. Soc.* 111:292 (1989), and shown schematically in FIG. 2. Anguibactin has a molecular weight of 348 g/mol, which is about half the molecular weight of deferoxamine (657 g/mol). Anguibactin can be regarded as a form of catechol rather than a monophenol. It has a unique structure which bears some resemblance to pyochelin. See Llinas et al., *Biochemistry* 12:3836 (1973). Anguibactin has been identified as ω-N-hydroxy-ω-[[2′-(2″,3″-dihydroxyphenyl)-thiazolin-4′-yl]-carboxy]histamine by crystal X-ray diffraction studies of its anhydro derivative, proton and $^{13}C$ nuclear magnetic resonance spectroscopy of its deferri and Ga(III) complex, fast-atom bombardment (FAB) mass spectrometry, and chemical degradation. As can be seen, the molecule contains catecholate and hydroxamate structures. Single-crystal structure determination of the Ga(III) complex (used instead of iron) of racemized anguibactin showed a 1:1 metal-to-ligand stoichiometry in which the O-hydroxy group, the nitrogen of the thiazolin ring, the hydroxamate (N-O group), and the deprotonated nitrogen of the imidazole ring coordinate the metal ion.

Each molecule of anguibactin chelates one ferric ($Fe^{3+}$ or Fe(III)) ion. Anguibactin also binds Ga(III). It is expected that anguibactin, similar to other siderophores such as ferrichrome and enterobactin that bind Fe(III) and Ga(III), can also bind Ai(III), but tests to determine this have not yet been performed. Anguibactin does not bind any metal other than iron known to be essential for bacterial metabolism. Also, anguibactin has only a very weak affinity for ferrous ($Fe^{2+}$) and $Ca^{2+}$ ions.

As expected, the ability of anguibactin to bind $F^{3+}$ is dependent on pH. However, excellent binding can be achieved even in mildly alkaline conditions. The affinity of anguibactin for ferric ions is extremely high, as evidenced by the ability of anguibactin to remove ferric ion from ferric hydroxide which is extremely insoluble in aqueous solutions at pH between 7 and 8 ($K_s < 10^{-38}M$). In competitive binding assays, anguibactin is able to remove $Fe^{3+}$ from other siderophores such as aerobactin, which has a deferrisiderophore formation constant (log $K_f$) of about 22.9, and from transferrin, which has a log $K_f$ value within the range of about 32 to about 36. Since deferoxamine has a deferrisiderophore formation constant of about 30.6, these data indicate that anguibactin is a more powerful iron chelator than the widely used deferoxamine.

The small size of anguibactin, relative to other siderophores such as deferoxamine, is believed to be a factor contributing to its strong ability to wrest Fe(III) from iron-transport and iron-storage proteins. Metal-protein bonds act over small distances and a bound metal ion is often buried in a cleft or the like in the protein molecule. Any successful "competitor" chelator must be able to penetrate to a position closely adjacent the protein-metal bond so as to disrupt it and permit the metal ion to pass over to the chelator. The smaller the chelator, the generally better its "penetrating" ability.

Anguibactin is freely soluble in water and methanol. Although acid hydrolyzable under certain acid conditions, the anguibactin molecule appears to remain intact at a pH as low as 3. Hydrochloric acid at a concentration of 6N will cleave anguibactin to 2,3-dihydroxybenzoic acid, dehydrocystine, and histamine.

Bacterial Production of Diffusible Anquibactin

A mutant strain of *Vibrio anguillarum* termed 775:Tn1-5 was produced which contained the pJM1-derivative plasmid pJHC-91 in which a transposon element Tn1 was inserted into genetic unit I. This mutant strain can grow in vitro in iron-limited media only if the supernatant from strains containing the wild-type pJM1 plasmid, and thus plenty of anguibactin, is supplied. Therefore, strains harboring the pJHC-91 plasmid must be able to transport and incorporate iron from anguibactin but are not able to produce this anguibactin itself. Strains containing the pJHC-91 plasmid are able to synthesize the pOM2 outer membrane protein.

Another mutant of *V. anguillarum*, 775:Tn1-6, harboring a variant of plasmid pJM1 termed pJHC9-8, lacks both the ability to synthesize anguibactin and the ability to use the siderophore when it is supplied from external sources. Plasmid pJHC9-8 is a derivative of pJM1 that resulted from Tn1 insertion and deletion of most of the iron-uptake region. Strains harboring pJHC9-8 not only lack the ability to produce anguibactin but also do not synthesize the pOM2 protein.

Experimental infections of salmonid fishes with mixtures consisting of a wild-type virulent strain of *V. anguillarum* and the siderophore-deficient, receptor-deficient mutant strain 775::Tn1-5 resulted in recovery of both the wild-type strain and the mutant strain, whereas infections with mixtures consisting of the wild-type virulent strain and the siderophore-deficient, receptor-deficient mutant 775::Tn1-6 resulted in recovery of only the wild-type strain. These results demonstrated that anguibactin is produced in vivo in a diffusible form by *V. anguillarum.*

The level of siderophore in the blood and kidneys of fish infected with the wild-type strain was sufficient to provide iron for considerable growth of the avirulent strain lacking the ability to produce the siderophore but possessing the transport functions. These results indicate that anguibactin is released from cells infected with *V. anguillarum*, encounters ferric iron bound to iron-transport proteins in the host's body, and forms a ferri-anguibactin complex by stripping Fe(III) from said proteins. The complex is then utilized by both wild-type bacteria and uptake-proficient bacteria after contact with a receptor protein to which the ferri-anguibactin complex binds.

Inhibition by Anguibactin of Iron Uptake by Cells

An experiment was conducted to characterize the chelation properties of anguibactin by examining its effect on iron uptake by mammalian cells in culture.

Normal human diploid fibroblast cells were mixed with $^{59}Fe$-containing cell-growth medium. Samples of the dosed cells were then incubated for increasing lengths of time. After each time period, the corresponding samples were rinsed to remove any free radioiron. The rinsed cells were treated with trypsin and the lysates precipitated with trichloroacetic acid. Radioactive counting of the precipitated lysates was performed using a Beckman counter. Addition of anguibactin and subsequent assay for radioiron in otherwise identical parallel samples yielded a measure of the capacity of the siderophore present in the cell-growth medium to interrupt the uptake of radioiron by the cultured cells. Results are shown in FIG. 3, which clearly shows that anguibactin interrupts the flow of iron into human cells.

A similar experiment performed using rat heart cells not yet "immortalized" for sustained growth under cell-culture conditions yielded substantially the same results (data not shown).

These results, considered in combination with the results of experiments demonstrating production of diffusible anguibactin able to wrest sufficient iron from tissues of a fish host sufficient for bacterial growth and virulence (supra), indicate that anguibactin is effective in inhibiting the iron uptake of cells of animals as diverse as humans, rats, and fish. As a result, anguibactin would be effective as a siderophore administered to a subject animal for the purpose of removing excess iron from the subject's body.

Toxicity of Anguibactin

Preliminary studies indicate that anguibactin toxicity is very low. Injection of 400 μl anguibactin into fish and 400 μl into rabbits showed no discernable adverse effect on the subjects. These results may be explained in part by the low affinity of anguibactin for $Ca^{2+}$. As is known in the art, calcium chelators such as EDTA are relatively toxic in part because they can cause a depletion of $Ca^{2+}$ in body fluids, where $Ca^{2+}$ is vital for many normal metabolic processes.

Evaluating Anguibactin for Use in Deferration Therapy

Since anguibactin is highly soluble in water, apparently has very low toxicity, has a molecular weight about half that of deferoxamine, impairs uptake of radioiron by living cells, and appears to chelate ferric iron even more strongly than deferoxamine, it is expected that anguibactin would be an effective siderophore for deferration therapy.

Similar to deferoxamine and other "hard"-base siderophores, anguibactin shows little affinity for "soft" acid cations such as $Fe^{2+}$. As a result, ferric iron can be released from the siderophore via a reduction step, wherein the chelated ferric iron is reduced to ferrous iron ($Fe^{2+}$) which is then released from the siderophore. Such release of iron prepares the molecules for use as an iron chelator drug. For example, sodium and potassium dithionites (hyposulfites), and sodium and potassium ascorbates are known in the art as suitable reducing agents, particularly for hydroxamates and phenolates or catecholates, respectively. Other candidate reducing agents are hydroquinone and hydroxylamine.

Anguibactin is administered in vivo to a subject as an aqueous solution, preferably by intramuscular or subcutaneous injection, in a regimen similar to that used for deferoxamine. For intramuscular or subcutaneous administration, anguibactin is prepared by dissolving the purified compound in pyrogen-free sterile water or isotonic saline at a concentration of about 250 mg/mL.

If administered intravenously, it should be added to a standard I.V. solution such as isotonic saline or aqueous glucose solution. For deferration therapy, the dose regimen would typically start out relatively high and then be reduced as therapy progresses. Siderophore dosages for human use typically range from 0.1 to 5 g, preferably 0.5 to 2.5 g, depending in part upon the age, weight, and degree of iron intoxication of the patient. With deferoxamine, 1.0 g is usually administered initially, followed by 500 mg every 4 hours, not to exceed 6.0 g in 24 hours. For a 200-pound person, these doses are equivalent to about 11 mg/kg, 5.5 mg/kg, and 2.75 mg/kg, respectively. Veterinary dosages are based on a g/kg weight ratio similar to that for humans. To minimize adverse effects from a too rapid removal of iron from the body, siderophore dosages should be spread out over time, where the concentration of siderophore in the body is maintained at a moderate level during the course of deferration therapy. A dosage regimen of about 15 mg/kg/hr for strong chelators is generally recognized as a maximum. Due to the low toxicity of anguibactin and its iron-binding behavior similar to other siderophores, it is expected that a similar dose regimen would be used for anguibactin when administered to humans.

To determine the ability to excrete chelated iron, a procedure similar to that generally used to evaluate iron chelators is employed. Trace amounts of $^{59}FeCl_3$ are incubated in vitro with about 10 mg anguibactin and subcutaneously injected into normal subjects such as rats. Cumulative excretion of radioiron is measured during the subsequent week in urine and feces. Weak iron chelators are not able enhance $^{59}Fe$ excretion relative to a control injected with $^{59}FeCl_3$ only. Strong chelators such as anguibactin and deferoxamine enhance excretion of radioiron. Evaluation of the distribution of radioiron in urine and stool provides an indication of whether the siderophore-bound iron is removed from plasma by kidneys (urine) or by the liver followed by excretion to the bile (stool).

To determine whether anguibactin functions to remove iron from the iron pool in the body, radioiron is administered to subjects, followed by an evaluation of the distribution of radioiron in the reticuloendothelial system and blood components. Again, anguibactin is administered as an aqueous solution. Appropriate radioprobes include $^{59}Fe$-ferritin and $^{59}Fe$-denatured red blood cells ($^{59}Fe$-DRBC) for targeting the parenchymal and reticuloendothelial iron stores, respectively.

Clinical conditions in which iron chelator therapy is employed are simulated by using hypertransfused subjects, such as rodents. For example, anguibactin is administered as a constant subcutaneous infusion at a rate of 0.1 mg/kg/hr in rats. Infusion is performed using an osmotic minipump implanted between the scapulae. The rate of fluid delivery of the osmotic pump is 10 microliters per hour. Infusion is started at the time of $^{59}Fe$ labeling and continued for 24 hours. Urine and stool are collected and the amount of radioiron excreted is determined. In separate experiments, anguibactin is administered orally followed by assessment of radioiron excretion in urine and stool.

Controls for both hypertransfused and orally-dosed subjects are non-dosed subjects as well as subjects receiving another siderophore such as deferoxamine at the same dose.

Hypertransfusions are performed by two intravenous infusions of 2 mL of packed cells suspended in 1 mL physiological saline per 100 g body weight of the subject. Infusions are made through a catheter placed in the right jugular vein under halothane anesthesia. The catheter can consist merely of a silastic tip inserted into the vein and welded to a length of polyethylene PE-50 tubing tunneled subcutaneously to exit at the nape of the neck. The catheters should be implanted at least 72 hours before beginning infusion. Infusions can be made using, for example, a Harvard infusion pump. Infusion of packed cells is performed at four days and again at one day before administration of radiolabeled iron.

$^{59}Fe$-DRBCs are prepared by injecting rats with 100–200 $\mu$Ci of $^{59}Fe$-citrate five days prior to harvesting the cells. The rats are then injected with 50–100 $\mu$Ci of $^{59}Fe$-citrate to maintain specific radioactivity at about 0.05 to 0.1 $\mu$Ci/mg hemoglobin. Blood is removed in volumes of about 1 mL. After washing the blood cells, the cells are resuspended and subjected to 40° C. for 15 min to heat-denature them. After heat-denaturation, the cells are washed again and suspended in saline buffer at a concentration of 5 mL per mL.

$^{59}Fe$-ferritin is prepared by injecting 10–200 $\mu$Ci of $^{59}Fe$-citrate into rats which have been given 12 mg of Fe-dextran 7 days before. After 24 hours, the rats are sacrificed and ferritin therefrom prepared according to the method of Bjorklid and Helgeland, *Biochem. Biophys. Acta* 221:583 (1970).

As stated hereinabove, the anguibactin molecule appears to be stable in pH environments as low as pH 3. Nevertheless, the molecule undergoes acid hydrolysis to at least a partial degree as the environment becomes more acidic. Since the pH of the stomach lumen is highly acidic, one way to administer anguibactin orally without the possibility of excessive acid hydrolysis occuring before the compound is absorbed in the gut is to encapsulate it into microcapsules able to pass through the stomach and dissociate in the small intestine. Similar methods are employed in the art for administering so-termed "time-release" pharmacological agents. For example, anguibactin could be encapsulated using an enteric coating applied around a tablet, a capsule, or individual particless, droplets, or granules. One method involves the use of gelatine capsules coated with cellulose acetate phthalate/diethylphthalate copolymer, which protects the gelatin from water under acid conditions such as found in the stomach. Under the neutral to slightly alkaline conditions found in the intestines, the coating becomes deprotonated and hence vulnerable to attack by water. Another coating example is polymeric hydrogels which are resistant dissociation under acidic conditions.

Immobilized Anguibactin

Anguibactin has a chemical structure that would enable it to be immobilized on an insoluble substrate and used, for example, in the construction of columns through which an iron-containing liquid is percolated for the purpose of removing iron therefrom. In this manner, for example, fluids could be deferrated outside a patient's body, where the fluid is either removed from the body via catheter or the like, passed through said column, then returned to the body, or passed as a therapeutic agent through said column to effect deferration before administration to the patient.

Binding of anguibactin to a substrate would in most cases require a bifunctional "spacer" or "linker" compound serving to chemically bond the siderophore to the sustrate in a manner known in the art of conjugating chemically active molecules to substrates. The linker should be bound to anguibactin in a location on the siderophore molecule not participating in the bonding of $Fe^{3+}$ or in a location that would not alter the configuration of the molecule and render it either incapable or weakly capable of chelating iron. Although linkers should be bifunctional, they need not have the same reactive group on each end.

To bond anguibactin to a substrate, it is important that molecules comprising the substrate have substituent groups available to participate in reactions by which anguibactin is conjugated via the linker to the substrate. Such groups can include carboxylic acid groups, amides, aldehydes, halogens, hydroxyls, sulfonates, azides, and other reactive groups known in the art that will react with complementary reactive groups on the linker molecules. In conjugating the anguibactin to the substrate, a reactive group on one end of the linker reacts with an available reactive group on the substrate; a reactive group on the other end of the linker reacts with the anguibactin in a manner wherein the siderophore retains its ability to bind iron. Representative reactions known in the art by which the linker becomes bonded to the substrate include formation of esters, amides; amino, amidino, or diazo linkages, ethers, sulfonamides, and the like. The linker can include a hydrocarbon or other chain serving to space the anguibactin, while bonded to the substrate, away from the substrate surface.

Suitable substrates for the above include hydrophilic gels such as agarose, alginate, and polyacrylamide, plastics such as polystyrene and nylon, glass, silica gel, ion exchange resins, carbohydrate polymers such as cellulose, dextran, and sephadex. The substrate is preferably in a particulate form or other form amenable to liquid percolation therethrough. A relatively high surface area is preferred to ensure a maximal number of conjugates.

Once the siderophore is bonded to the substrate, the substrate is typically packed into one or more columns through which the liquid to be deferrated is passed for the purpose of iron removal. Representative areas in which such a technology could be used is in deferration of hemodialysate (wherein iron in dialysate has been known to cause precipitation problems in dialysis equipment) and of liquid pharmaceuticals. Since many bacteria are dependent on a source of iron for growth, removal of virtually all the iron from a liquid pharmaceutical or other liquid such as for food or cosmetic use can render the liquid much less able to support bacterial growth and, therefore, more resistant to certain types of spoilage.

Having described the principles of my invention with reference to several preferred embodiments, it should be apparent to those of ordinary skill in the art that the invention may be modified in arrangement and detail without departing from such principles. I claim as my invention all such modifications as come within the true spirit and scope of the following claims.

I claim:

1. A method for inhibiting the uptake of ferric iron by a population of living eukaryotic animal cells that is in contact with an aqueous medium comprising ferric iron, the method comprising:

adding anguibactin having substantially no bound ferric iron to the aqueous medium in an amount sufficient to chelate at least a portion of the ferric iron in the aqueous medium; and after adding the anguibactin, incubating the cells contacted by said medium for a time sufficient for the anguibactin to chelate at least a portion of the ferric iron in the aqueous medium, thereby rendering said ferric iron unavailable for uptake by said cells.

2. A method for reducing the concentration of ferric iron present in a vertebrate animal subject, the method comprising:

adding anguibactin having substantially no bound ferric iron to an aqueous carrier liquid physiologically acceptable to said animal subject to form an aqueous pharmacological solution of anguibactin; and administering at least one dose of said aqueous solution of anguibactin to said animal subject to chelate at least a portion of the ferric iron present in said animal subject.

3. A method as recited in claim 2 wherein the anguibactin is added to pyrogen-free sterile water serving as said aqueous carrier liquid.

4. A method as recited in claim 2 wherein the anguibactin is added to pyrogen-free sterile isotonic saline solution serving as said aqueous carrier liquid.

5. A method as recited in claim 2 wherein the anguibactin is administered subcutaneously to said animal subject.

6. A method as recited in claim 2 wherein the anguibactin is administered intramuscularly to said animal subject.

7. A method for reducing the concentration of ferric iron present in the body of a vertebrate animal subject, comprising orally administering at least one pharmacologically effective dose of anguibactin that has been treated in a manner serving to protect the anguibactin from hydrolysis under acid conditions and make the anguibactin available for absorption into the body of said animal subject under neutral and alkaline conditions.

* * * * *

UNITED STATES PATENT AND TRADEMARK OFFICE
CERTIFICATE OF CORRECTION

PATENT NO. : 5,393,777
DATED : February 28, 1995
INVENTOR(S) : JORGE H. CROSA

It is certified that error appears in the above-identified patent and that said Letters Patent is hereby corrected as shown below:

Column 1, line 32, "Pseudomonas" should be --*Pseudomonas*--.

Column 1, line 34, "Actinomyces" should be --*Actinomyces*--.

Column 1, line 36, "Penicillium" should be --*Penicillium*--.

Column 1, line 37, "Rhodoturula" should be --*Rhodoturula*--.

Column 1, line 38, "Ectomycorrhiza" should be --*Ectomycorrhiza*--.

Column 6, line 44, "Ai(III)" should be --Al(III)--.

Signed and Sealed this

Twenty-sixth Day of December, 1995

Attest:

BRUCE LEHMAN

*Attesting Officer*  Commissioner of Patents and Trademarks